United States Patent
Utsumi

(10) Patent No.: US 8,592,081 B2
(45) Date of Patent: Nov. 26, 2013

(54) NONAQUEOUS SECONDARY BATTERY AND FLAME RETARDANT FOR THE SAME

(75) Inventor: Hisayuki Utsumi, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 51 days.

(21) Appl. No.: 13/088,666

(22) Filed: Apr. 18, 2011

(65) Prior Publication Data

US 2011/0256457 A1    Oct. 20, 2011

(30) Foreign Application Priority Data

Apr. 19, 2010    (JP) ................. 2010-096297

(51) Int. Cl.
*H01M 10/056*    (2010.01)
(52) U.S. Cl.
USPC ........................................... 429/188
(58) Field of Classification Search
None
See application file for complete search history.

(56) References Cited

U.S. PATENT DOCUMENTS

| | | |
|---|---|---|
| 5,753,389 A | 5/1998 | Gan et al. |
| 2001/0004507 A1 | 6/2001 | Gan et al. |
| 2010/0035146 A1 | 2/2010 | Fujii et al. |

FOREIGN PATENT DOCUMENTS

| | | | |
|---|---|---|---|
| CN | 101548425 | | 9/2009 |
| EP | 0996187 A | * | 4/2000 |
| JP | H10-050325 A | | 2/1998 |
| JP | 11-329495 | | 11/1999 |
| JP | 2000-133306 A | | 5/2000 |
| JP | 2001-338682 | | 12/2001 |
| JP | 2001-525597 | | 12/2001 |
| JP | 2002-208434 A | | 7/2002 |
| JP | 2007200605 A | * | 8/2007 |
| WO | WO 99/28987 | | 6/1999 |

OTHER PUBLICATIONS

Machine translation of JP2007200605A.*

* cited by examiner

*Primary Examiner* — Patrick Ryan
*Assistant Examiner* — Wyatt McConnell
(74) *Attorney, Agent, or Firm* — Nixon & Vanderhye P.C.

(57) ABSTRACT

A nonaqueous secondary battery, comprising: a positive electrode; a negative electrode; and a nonaqueous electrolyte solution, the nonaqueous electrolyte solution containing as a flame retardant a compound of the general formula (I):

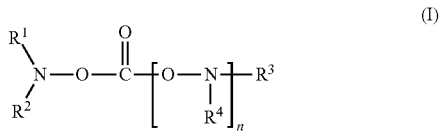

wherein $R^1$ and $R^2$, which are the same or different, each represents a group that is selected from a hydrogen atom, a lower alkyl, lower alkenyl, lower alkoxy, lower alkoxycarbonyl, lower alkylcarbonyl, lower cycloalkyl or aryl group, and that may have a substituent, or $R^1$ and $R^2$ taken together are a methylene group that may have a substituent, or $R^1$ and $R^2$ taken together form a ring structure containing a nitrogen atom to which $R^1$ and $R^2$ are attached, the ring structure being a five-membered or six-membered hydrocarbon ring that may have one or two oxo groups, or a five-membered or six-membered heterocycle that may further contain a nitrogen atom; n is 0 or 1; when n is 0, $R^3$ is a group that is selected from a hydrogen atom, a halogen atom, a lower alkyl, lower alkenyl, lower alkoxy, lower alkoxycarbonyl, lower alkylcarbonyl, lower cycloalkyl or aryl group, and that may have a substituent; and when n is 1, $R^3$ and $R^4$ are as defined for $R^1$ and $R^2$.

6 Claims, No Drawings

NONAQUEOUS SECONDARY BATTERY AND FLAME RETARDANT FOR THE SAME

CROSS-REFERENCE TO RELATED APPLICATIONS

This application is related to Japanese Patent Application No. 2010-96297 filed on Apr. 19, 2010 whose priority is claimed under 35 USC §119, the disclosure of which is incorporated by reference in its entirety.

BACKGROUND OF THE INVENTION

1. Field of the Invention

The present invention relates to a nonaqueous secondary battery and a flame retardant for the battery. More particularly, the present invention relates to a nonaqueous secondary battery that has battery performance comparable to conventional batteries and that is superior in safety to conventional batteries, and a flame retardant for the battery.

2. Description of the Related Art

In recent years, reduction in size and weight of electronic devices has been remarkably progressed, and with the progress, it has been demanded that secondary batteries that are used for such electronic devices should have higher energy density. An example of secondary batteries that can meet the demand is a secondary battery including a nonaqueous electrolyte solution (hereinafter, referred to as nonaqueous secondary battery) such as a lithium-ion secondary battery.

The lithium-ion secondary battery includes a nonaqueous electrolyte solution, and the nonaqueous electrolyte solution comprises an electrolyte salt such as a lithium salt and a nonaqueous solvent. The nonaqueous solvent is desired to have high dielectric constant and high oxidation potential, and to be stable in batteries regardless of operation environment.

As such a nonaqueous solvent, aprotic solvents are used, and known examples thereof include high-permittivity solvents such as cyclic carbonates including ethylene carbonate and propylene carbonate, and cyclic carboxylate esters including γ-butyrolactone; and low-viscosity solvents such as chain carbonates including diethyl carbonate and dimethyl carbonate, and ethers including dimethoxyethane. Usually, a high-permittivity solvent and a low-viscosity solvent are used in combination.

However, the lithium-ion secondary battery including a nonaqueous electrolyte solution may suffer from leakage of the nonaqueous electrolyte solution due to a defect involving increased internal pressure caused by breakage of the battery or any other reason. The leakage of the nonaqueous electrolyte solution may lead to short-circuit between a positive electrode and a negative electrode constituting the lithium-ion secondary battery to cause generation of fire or burning. It may also lead to generation of heat in the lithium-ion secondary battery to cause vaporization and/or decomposition of the organic solvent-based nonaqueous solvent to produce gas. In some cases, the produced gas caught fire or caused rupture of the lithium-ion secondary battery. In order to solve the above-described problems, studies have been carried out to give flame retardancy by adding a flame retardant to the nonaqueous electrolyte solution.

Techniques to add a flame retardant to a nonaqueous electrolyte solution is proposed in Japanese Unexamined Patent Publication No. 2001-338682, Japanese Unexamined Patent Publication (Translation of PCT Application) No. 2001-525597 and Japanese Unexamined Patent Publication No. HEI 11 (1999)-329495, for example.

As the flame retardant, specifically, Japanese Unexamined Patent Publication No. 2001-338682 proposes phosphazene derivatives, Japanese Unexamined Patent Publication No. 2001-525597 proposes azobis(isobutyronitrile) (AIBN), and Japanese Unexamined Patent Publication No. HEI 11 (1999)-329495 proposes imidazole compounds.

While producing excellent flame retardancy, phosphazene derivatives are expected to cause unstable operation of the lithium-ion secondary battery when used with certain kinds of nonaqueous solvents or blended with a nonaqueous solvent at certain blending ratios, and when used in a certain temperature environment, in particular, at high temperature. Generally, when the lithium-ion secondary battery generates heat for some reasons, thermal decomposition reaction occurs at an interface between a negative electrode or a positive electrode and the electrolyte solution, and in the case of thermal runaway of this reaction, the lithium-ion secondary battery may be ruptured or catch fire. This phenomenon can occur even when a phosphazene derivative is blended. In addition, since the phosphazene derivative becomes a membrane on the surface of the negative electrode, battery characteristics such as cycle characteristics and environmental stability in operation may be degraded.

In an Example in Japanese Unexamined Patent Publication No. 2001-338682, a phosphazene derivative is used in a high content of 40% by volume with respect to a nonaqueous solvent. Since the phosphazene derivative has relatively high viscosity and relatively low dielectric constant, operation of a battery having a high phosphazene derivative content in a low-temperature environment causes concern about reduction in the electric conductivity of the nonaqueous electrolyte solution and degradation in the battery performance due to the reduction.

Meanwhile, AIBN is less soluble in nonaqueous solvents typified by aprotic solvents, and therefore the content thereof cannot be increased. Accordingly, AIBN may not improve flame retardancy sufficiently. Furthermore, AIBN may be electrolyzed due to charge and discharge of the lithium-ion secondary battery, causing concern about degradation in battery performance.

Likewise, imidazole compounds do not produce sufficient flame retardancy unless the content thereof is increased. However, an increased content thereof causes concern about degradation in the cycle characteristics and the environmental stability in operation.

It is therefore desired to further improve flame retardancy without degrading battery performance.

SUMMARY OF THE INVENTION

According to an aspect of the present invention, therefore, there is provided a nonaqueous secondary battery, comprising: a positive electrode; a negative electrode; and a nonaqueous electrolyte solution, the nonaqueous electrolyte solution containing as a flame retardant a compound of the general formula (I):

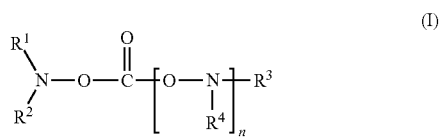

wherein $R^1$ and $R^2$, which are the same or different, each represents a group that is selected from a hydrogen atom, a lower alkyl, lower alkenyl, lower alkoxy, lower alkoxycarbonyl, lower alkylcarbonyl, lower cycloalkyl or aryl group, and that may have a substituent, or $R^1$ and $R^2$ taken together are a methylene group that may have a substituent, or $R^1$ and $R^2$ taken together form a ring structure containing a nitrogen atom to which $R^1$ and $R^2$ are attached, the ring structure being a five-membered or six-membered hydrocarbon ring that may have one or two oxo groups, or a five-membered or six-membered heterocycle that may further contain a nitrogen atom; n is 0 or 1; when n is 0, $R^3$ is a group that is selected from a hydrogen atom, a halogen atom, a lower alkyl, lower alkenyl, lower alkoxy, lower alkoxycarbonyl, lower alkylcarbonyl, lower cycloalkyl or aryl group, and that may have a substituent; and when n is 1, $R^3$ and $R^4$ are as defined for $R^1$ and $R^2$.

According to another aspect of the present invention, there is provided a flame retardant for a nonaqueous secondary battery comprising a compound of the general formula (I)

The inventor of the present invention has made intensive studies about flame retardants for nonaqueous secondary batteries and, as a result, unexpectedly found that a battery is enabled to produce sufficient flame retardancy when a nonaqueous electrolyte solution therein contains a "compound having, in the molecule, a carbonyl group to which a functional group having a nitrogen-oxygen bond is attached", to achieve the present invention. As a result of the sufficient flame retardancy thus produced, safety and reliability of the nonaqueous secondary battery can be ensured even when the battery is abnormally heated. Furthermore, this flame retardant does not affect electric characteristics of the nonaqueous secondary battery over a wide temperature range to allow provision of a nonaqueous secondary battery showing stable cycle characteristics.

DESCRIPTION OF THE PREFERRED EMBODIMENTS

A nonaqueous secondary battery of the present invention comprises: a positive electrode; a negative electrode; and a nonaqueous electrolyte solution, and the nonaqueous electrolyte solution contains as a flame retardant a compound having a structure represented by the general formula (1).

In the present invention, a nonaqueous secondary battery is enabled to produce sufficient flame retardancy by including a "compound having, in the molecule, a carbonyl group to which a functional group having a nitrogen-oxygen bond is attached" in a nonaqueous electrolyte solution. As a result, risk of thermal runaway can be reduced even in an abnormal situation such as where the internal temperature of the nonaqueous secondary battery rises due to short-circuit, overcharge or any other reasons. In addition, this compound has less impact on electric characteristics of the nonaqueous secondary battery including cycle characteristics. Accordingly, it is possible to provide a nonaqueous secondary battery, improved in safety and reliability.

In addition, when the compound represented by the general formula (I) is contained in the nonaqueous electrolyte solution in a proportion of 1% by volume to 60% by volume, when the compound represented by the general formula (I) is a compound that produces inert gas containing $CO_2$ or CO as a main component when heated at a temperature higher than its decomposition temperature, when the compound represented by the general formula (I) is a compound having a decomposition temperature of 120° C. to 250° C., or when the compound represented by the general formula (I) is N-acetoxy-N-methyl-acetamide, succuinimidyl acrylate, acetoxime benzoate or di(N-succinimidyl) carbonate, the above-described effects will be produced more advantageously.

Furthermore, because of the above-described effects, it is possible to provide a flame retardant for a nonaqueous secondary battery, the flame retardant being capable of improving the safety and the reliability of the nonaqueous secondary battery.

The inventor believes that the mechanism for the "compound having, in the molecule, a carbonyl group to which a functional group having a nitrogen-oxygen bond is attached" used in the present invention as a flame retardant to exert flame retardancy is as follows: in the case of thermal runaway, which starts fire, of the nonaqueous secondary battery, thermal decomposition is caused to generate inert gas containing $CO_2$ or CO as a main component and, as a result, reduce the ambient oxygen concentration thereby to extinguish the fire (anoxic extinction). In order to achieve such a mechanism, it is essential that the compound of the present invention has, in the molecule, the "carbonyl group to which a functional group having a nitrogen-oxygen bond is attached".

Hereinafter, the compound represented by the general formula (I), that is, the "compound having, in the molecule, a carbonyl group to which a functional group having a nitrogen-oxygen bond is attached" will be also referred to as "compound of the present invention".

The compound of the present invention is represented by the general formula (I):

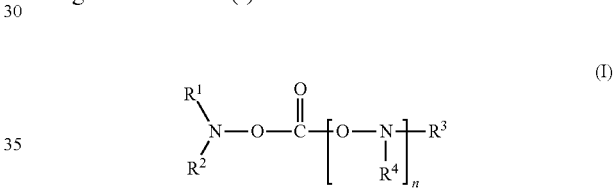

wherein $R^1$ and $R^2$, which are the same or different, each represent a group that is selected from a hydrogen atom, lower alkyl, lower alkenyl, lower alkoxy, lower alkoxycarbonyl, lower alkylcarbonyl, lower cycloalkyl or aryl group, and that may have a substituent.

In the present invention, the term "lower" means 1 to 6 carbon atoms. In the case of the cycloalkyl group, however, the term "lower" means 3 to 6 carbon atoms.

As the lower alkyl group, may be mentioned linear or branched alkyl group having 1 to 6 carbon atoms. Specific examples thereof include methyl, ethyl, n-propyl, isopropyl, n-butyl, isobutyl, sec-butyl, tert-butyl, n-pentyl, isopentyl, neopentyl, tert-pentyl, n-hexyl and isohexyl groups. Out of them, alkyl group having 1 to 4 carbon atoms is preferable, and methyl and tert-butyl groups are particularly preferable.

As the lower alkenyl group, may be mentioned linear or branched alkenyl group having 1 to 6 carbon atoms, out of which linear alkyl group having 1 to 4 carbon atoms is preferable. Specific examples thereof include vinyl, 1-propenyl, allyl (2-propenyl), 1-butenyl, 2-butenyl and 3-butenyl groups. Out of them, vinyl group is particularly desirable.

As the lower alkoxy group, may be mentioned linear or branched alkoxy group having 1 to 6 carbon atoms. Specific examples thereof include methoxy, ethoxy, n-propoxy, isopropoxy, n-butoxy, isobutoxy, sec-butoxy, tert-butoxy, n-pentyloxy, isopentyloxy, neopentyloxy, tert-pentyloxy, n-hexyloxy and isohexyloxy groups. Out of them, alkoxy group having 1 to 4 carbon atoms is preferable, and methoxy group is particularly preferable.

The lower alkoxycarbonyl group is group which is derived from a lower fatty acid and in which an alcohol residue is removed. Specific examples thereof include formyloxy, acetoxy, propionyloxy, butyryloxy, isobutyryloxy, valeryloxy, isovaleryloxy and pivaloyloxy groups. Out of them, alkoxycarbonyl group having 1 to 4 carbon atoms is preferable, and acetoxy group is particularly preferable.

The lower alkyl carbonyl group is acyl group derived from a lower fatty acid, that is, lower fatty acyl group. Specific examples thereof include formyl, acetyl, propionyl, butyryl, isobutyryl, valeryl, isovaleryl and pivaloyl groups. Out of them, alkylcarbonyl group having 1 to 4 carbon atoms is preferable, and acetyl group is particularly preferable.

As the cycloalkyl group may be mentioned cycloalkyl group having 3 to 6 carbon atoms. Specific examples thereof include cyclopropyl, cyclobutyl, cyclopentyl and cyclohexyl groups. Out of them, cycloalkyl group having 3 or 4 carbon atoms is preferable, and cyclopropyl and cyclobutyl groups are particularly preferable.

As the aryl group, may be mentioned aryl group having 6 to 10 carbon atoms. Specific examples thereof include phenyl, 1-naphthyl and 2-naphthyl groups. Out of them, phenyl and 2-naphthyl groups are particularly preferable.

Examples of the substituent that $R^1$ and $R^2$ may have include halogen atoms such as a fluorine atom, a chlorine atom and a bromine atom; lower alkyl group as described above; lower alkoxy group as described above; aryl group as described above; and aryloxy group.

Examples of the group that may have a substituent include p-tolyl group.

Alternatively, $R^1$ and $R^2$ taken together are a methylene group that may have a substituent. Examples of the methylene group that may have a substituent include isopropylidene group.

Alternatively, $R^1$ and $R^2$ taken together form a ring structure containing a nitrogen atom to which $R^1$ and $R^2$ are attached, and the ring structure is a five-membered or six-membered hydrocarbon ring that may have one or two oxo groups, or a five-membered or six-membered heterocyclic ring that may further contain a nitrogen atom.

Examples of the ring structure to be formed by $R^1$ and $R^2$ include cyclic amino group, cyclic lactam group, succinimide ring and imidazole ring. Out of them, succinimide and imidazole rings are particularly preferable.

In the general formula (I), n is 0 or 1.

When n is 0, $R^3$ is a group that is selected from a hydrogen atom, a halogen atom, lower alkyl, lower alkenyl, lower alkoxy, lower alkoxycarbonyl, lower alkylcarbonyl, lower cycloalkyl and aryl groups, and that may have a substituent.

When n is 0, it means that $R^3$ is directly attached to the carbon atom of the carbonyl group in the general formula (I).

Examples of the halogen atom include a fluorine atom, a chlorine atom and a bromine atom. Out of them, a chlorine atom and a fluorine atom are preferable, and a chlorine atom is particularly preferable.

Examples of the lower alkyl, the lower alkenyl, the lower alkoxy, the lower alkoxycarbonyl, the lower alkylcarbonyl, the lower cycloalkyl and the aryl groups to be selected as $R^3$, and the substituent that $R^3$ may have include those mentioned for $R^1$ and $R^2$.

As $R^3$, methyl, vinyl, isopropoxy and phenyl groups are particularly preferable.

When n is 1, $R^3$ and $R^4$ are as defined for $R^1$ and $R^2$.

The compound of the present invention has one "functional group having a nitrogen-oxygen bond" attached to the carbonyl group in the molecule when n is 0, and two "functional groups having a nitrogen-oxygen bond" when n is 1.

Examples of the compound of the present invention when n is 0 include N-acetoxy-N-methyl-acetamide, succuinimidyl acrylate [N-acryloyloxysuccinimide], acetoxime benzoate, N-tert-butyl-N-acetoxyaniline, N-acetyloxy-N-(p-tolyl)acetamide, N-acetoxy-N-phenylcarbamic acid isopropyl ester and N-acetoxy-N-(2-naphthyl)acetamide. Out of them, particularly preferable are N-acetoxy-N-methyl-acetamide wherein $R^1$ is an N-acetyl group, and $R^2$ and $R^3$ are methyl groups; succinimidyl acrylate wherein $R^3$ is a vinyl group, and $R^1$ and $R^2$ form a succinimide ring; and acetoxime benzoate wherein $R^1$ and $R^2$ taken together are an isopropylidene group, and $R^3$ is a phenyl group, because they decompose and produce inert gas containing $CO_2$ or $CO$ as a main component at a high rate in an abnormal situation.

Examples of the compound of the present invention when n is 1 include di(N-succinimidyl) carbonate and 1,1'-(Carbonylbisoxy)bis(1H-imidazole). Out of them, particularly preferable is di(N-succinimidyl) carbonate wherein $R^1$ and $R^2$ attached to a nitrogen atom form a succinimide ring, and $R^3$ and $R^4$ attached to a nitrogen atom form a succinyl ring, because they decompose and produce inert gas containing $CO_2$ or $CO$ as a main component at a high rate in an abnormal situation Solubility of the compound of the present invention in an aprotic solvent can be controlled by controlling the kinds of $R^1$ to $R^4$, for example. Accordingly, the compound of the present invention is enabled to have no effect on the electric characteristics of the nonaqueous secondary battery in a normal situation and to decompose to produce inert gas containing $CO_2$ or $CO$ as a main component thereby to control thermal runaway in an abnormal situation. The solubility can be increased by increasing the number of carbon atoms of $R^1$ to $R^4$ or using an aromatic group, for example.

Preferably, the compound of the present invention is a compound that produces inert gas containing $CO_2$ or $CO$ as a main component when heated at a temperature higher than its decomposition temperature. The decomposition temperature is preferably 100° C. or more higher than normal ambient temperature where the nonaqueous secondary battery is used. Specifically, the decomposition temperature is preferably 100° C. to 300° C. higher than the normal ambient temperature, and more preferably 120° C. to 250° C. higher than the normal ambient temperature, and still more preferably 140° C. to 250° C. higher than the normal ambient temperature.

When the difference between the decomposition temperature and the normal ambient temperature is less than 100° C., the compound of the present invention may decompose during normal use, and in this case, the electric characteristics of the nonaqueous secondary battery will be degraded.

Here, the decomposition temperature can be controlled by controlling substituent effects.

The compound of the present invention can be produced by commonly known methods or may be commercially available products as described in Examples.

The nonaqueous electrolyte solution contains an electrolyte salt, a nonaqueous solvent and, optionally, an additive. The compound of the present invention can function as a nonaqueous solvent. When the compound of the present invention by itself can provide a nonaqueous electrolyte solution having sufficient properties, therefore, no additional organic solvent needs to be used. However, in terms of enhancement in charge/discharge characteristics and resistance to low temperature of the nonaqueous secondary battery, the nonaqueous solvent is preferably a mixed solvent with an additional organic solvent.

As the additional organic solvent, aprotic organic solvents can be usually used. Examples of the aprotic organic solvents include, but not particularly limited to, dimethyl carbonate, diethyl carbonate, ethyl methyl carbonate, dipropyl carbonate, propylene carbonate, ethylene carbonate, butylene carbonate, γ-butyrolactone, γ-valerolactone, tetrahydrofuran, 2-methyltetrahydrofuran, dimethyl sulfoxide, 1,3-dioxolane, formamide, dimethylformamide, acetonitrile, methyl formate, methyl acetate, diethyl ether, 1,2-dimethoxyethane, 1,2-diethoxyethane, ethoxymethoxyethane, dioxane, sulfolane and methylsulfolane. One or more kinds of these organic solvents may be used independently or in combination.

The percentage of the compound of the present invention to be blended in the nonaqueous electrolyte solution is usually in a range of 1% to 60% (v/v), and preferably in a range of 10% to 40% by volume fraction. When the percentage is less than 1%, rupture and generation of fire of the nonaqueous secondary battery may not be sufficiently inhibited. On the other hand, when the percentage is more than 60%, the performance of the nonaqueous secondary battery may be deteriorated in a low-temperature environment.

As the electrolyte salt, a lithium salt is usually used. The lithium salt is not particularly limited, as long as it dissolves in the nonaqueous solvent. Examples thereof include $LiClO_4$, LiCl, $LiBF_4$, $LiPF_6$, $LiAsF_6$, $LiSbF_6$, $LiN(SO_2CF_3)_2$, $LiC(SO_2CF_3)_2$, lower aliphatic carboxylic acid, chloroborane lithium and 4-phenyllithium borate. One or more kinds of these lithium salts can be used independently or in combination. The amount of the electrolyte salt to be added is preferably 0.1 mol to 3 mol, and more preferably 0.5 mol to 2 mol with respect to 1 kg of the nonaqueous solvent.

Examples of the additive include conventionally known dehydrators and deoxidizers. Specific examples thereof include vinylene carbonate, fluoroethylene carbonate, trifluoropropylene carbonate, phenyl ethylene carbonate, succinic anhydride, glutaric anhydride, maleic anhydride, ethylene sulfite, 1,3-propane sultone, 1,4-butane sultone, methyl methanesulphonate, dibutylsulphide, heptane, octane and cycloheptane. They are usually contained in the nonaqueous solvent at a concentration of 0.1% by weight or more to 5% by weight or less. Then, the capacity maintenance characteristics and the cycle characteristics after storage in a high-temperature environment can be improved.

The positive electrode can be produced by applying, drying and pressurizing a paste containing, for example, a positive-electrode active material, a conductive material, a binder and an organic solvent on a positive-electrode current collector. The conductive material in an amount of 1 part by weight to 20 parts by weight, the binder in an amount of 1 part by weight to 15 parts by weight and the organic solvent in an amount of 30 parts by weight to 60 parts by weight can be blended with respect to 100 parts by weight of the positive-electrode active material.

Examples of the positive-electrode active material usable here include lithium compound oxides such as $LiNiO_2$, $LiCoO_2$ and $LiMn_2O_4$; and compounds obtained by substituting one or more elements in these oxides with other elements (for example, Fe, Si, Mo, Cu and Zn).

Examples of the conductive material include carbonaceous materials such as acetylene black and ketjen black.

Examples of the binder include polyvinylidene fluoride (PVdF), polyvinyl pyridine and polytetrafluoroethylene.

Examples of the organic solvent include N-methyl-2-pyrrolidone (NMP) and N,N-dimethylformamide (DMF).

Examples of the positive-electrode current collector include a foil or a thin sheet of a conductive metal such as SUS and aluminum.

The negative electrode can be produced by applying, drying and pressurizing a paste containing, for example, a negative-electrode active material, a conductive material, a binder and an organic solvent on a negative-electrode current collector. The conductive material in an amount of 1 part by weight to 15 parts by weight, the binder in an amount of 1 part by weight to 10 parts by weight and the organic solvent in an amount of 40 parts by weight to 70 parts by weight can be blended with respect to 100 parts by weight of the negative-electrode active material.

Examples of the negative-electrode active material include pyrolyzed carbons, cokes, graphites, vitreous carbons, sintered organic polymer compounds, carbon fibers and activated carbons.

Examples of the conductive material include carbonaceous materials such as acetylene black and ketjen black.

Examples of the binder include polyvinylidene fluoride, polyvinyl pyridine and polytetrafluoroethylene.

Examples of the organic solvent include N-methyl-2-pyrrolidone (NMP) and N,N-dimethylformamide (DMF).

Examples of the negative-electrode current collector include a foil of a metal such as copper.

Usually, a separator is interposed between the negative electrode and the positive electrode.

The material of the separator is usually a porous film, selected in view of solvent resistance and reducibility resistance. Suitable examples thereof include a porous film and a nonwoven fabric of polyolefin resin such as polyethylen and polypropylene. The film and the nonwoven fabric of such materials may be used as a single layer or multiple layers. In the case of multiple layers, it is preferable that at least one sheet of a nonwoven fabric is used in view of the cycle characteristics, performance at low temperature and load characteristics.

The separator is optionally interposed between the negative electrode and the positive electrode, and then a nonaqueous electrolyte solution is injected thereto to obtain a nonaqueous secondary battery. In addition, this nonaqueous secondary battery, as a unit, may be stacked into multiple layers.

Other than those mentioned, generally used and commonly known members can be used to constitute the nonaqueous secondary battery.

In addition, the form of the nonaqueous secondary battery is not particularly limited, and examples thereof include various forms such as a button type, a coin type, a rectangular type, a cylinder type having a spiral structure and a laminate type, which can be varied in size such as a thin type and a large size according to use.

EXAMPLES

Hereinafter, the present invention will be described in detail with reference to examples and comparative examples; however, the present invention is not limited to the following examples and comparative examples at all.

Example 1

To 80 ml of a mixed solvent of ethylene carbonate and diethylene carbonate (mixing ratio (volume ratio): ethylene carbonate/diethylene carbonate=1/2) (aprotic organic solvent), 20 ml of N-acetoxy-N-methyl-acetamide (product by Sigma-Aldrich Co., shown as "A" in Table 1) represented by the following formula was added as a compound of the present invention. In the mixed solvent obtained, $LiPF_6$ as a lithium salt was dissolved at a concentration of 1.0 mol/kg to prepare a nonaqueous electrolyte solution.

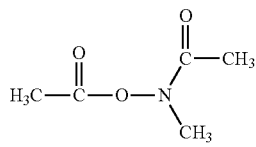

LiMn$_2$O$_4$ as a positive-electrode active material in an amount of 100 parts by weight, acetylene black as a conductive material in an amount of 5 parts by weight, PVdF as a binder in an amount of 5 parts by weight and NMP as a solvent in an amount of 40 parts by weight were kneaded for dispersion with a planetary mixer to prepare a paste for positive electrode formation. The paste prepared was applied with a coater to uniformly coat both sides of a band-like aluminum foil having a thickness of 20 μm constituting a positive-electrode current collector. Here, an end portion of the aluminum foil was left uncoated for connection of a terminal. The coat was dried under vacuum at 130° C. for 8 hours to remove the solvent, and then pressed by using a hydraulic press machine to form a positive plate. The positive plate obtained was cut into a predetermined size for use.

A natural powdered graphite manufactured in China as a negative-electrode active material (average particle diameter: 15 μm) in an amount of 100 parts by weight, vapor grown carbon fiber (VGCF) powder (VGCF, high-bulk-density product by Showa Denko K.K.) as a conductive material in an amount of 2 parts by weight, PVdF as a binder in an amount of 2 parts by weight and NMP as a solvent in an amount of 50 parts by weight were kneaded for dispersion with a planetary mixer to prepare a paste for negative electrode formation. The paste prepared was applied with a coater to uniformly coat both sides of a copper foil having a thickness of 10 μm constituting a negative-electrode current collector. Here, an end portion of the copper foil was left uncoated for connection of a terminal. Further, the coat was dried under vacuum at 100° C. for 8 hours to remove the solvent, and then pressed by using a hydraulic press machine to form a negative plate. The negative plate obtained was cut into a predetermined size for use.

The positive and negative plates obtained were stacked to form a laminate with a polypropylene porous film as a separator interposed therebetween, and then the nonaqueous electrolyte solution was injected into the laminate to produce a nonaqueous secondary battery.

Example 2

A nonaqueous secondary battery was produced in the same manner as in Example 1 except that the amount of the mixed solvent of ethylene carbonate and diethylene carbonate was changed to 99 ml, and the amount of the N-acetoxy-N-methyl-acetamide (product by Sigma-Aldrich Co.) used as the compound of the present invention was changed to 1 ml.

Example 3

A nonaqueous secondary battery was produced in the same manner as in Example 1 except that the amount of the mixed solvent of ethylene carbonate and diethylene carbonate was changed to 40 ml, and the amount of the N-acetoxy-N-methyl-acetamide (product by Sigma-Aldrich Co.) used as the compound of the present invention was changed to 60 ml.

Example 4

A nonaqueous secondary battery was produced in the same manner as in Example 1 except that the amount of the mixed solvent of ethylene carbonate and diethylene carbonate was changed to 90 ml, and 10 ml of succuinimidyl acrylate (product by Sigma-Aldrich Co., shown as "B" in Table 1) represented by the following formula was used as the compound of the present invention.

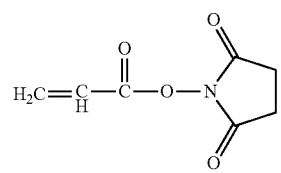

Example 5

A nonaqueous secondary battery was produced in the same manner as in Example 1 except that the amount of the mixed solvent of ethylene carbonate and diethylene carbonate was changed to 90 ml, and 10 ml of di(N-succinimidyl) carbonate (product by Tokyo Chemical Industry Co., Ltd., shown as "C" in Table 1) represented by the following formula was used as the compound of the present invention.

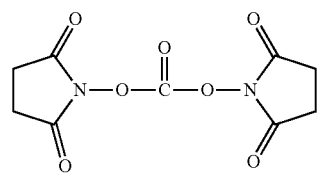 [SMILES: O=C(ON1C(=O)CCC1=O)ON1C(=O)CCC1=O]

Example 6

A nonaqueous secondary battery was produced in the same manner as in Example 1 except that the amount of the mixed solvent of ethylene carbonate and diethylene carbonate was changed to 90 ml, and 10 ml of acetoxime benzoate (product by Tokyo Chemical Industry Co., Ltd., shown as "D" in Table 1) represented by the following formula was used as the compound of the present invention.

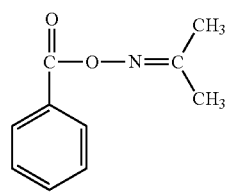

Comparative Example 1

A nonaqueous secondary battery was produced in the same manner as in Example 1, except that no compound of the present invention was used.

Comparative Example 2

A nonaqueous secondary battery was produced in the same manner as in Example 1 except that the amount of the mixed solvent of ethylene carbonate and diethylene carbonate was changed to 98 ml, and 2 ml of AIBN (azobisisobutyronitrile, product by Tokyo Chemical Industry Co., Ltd.) was used instead of the compound of the present invention.

Method for Testing Battery Performance

The nonaqueous secondary batteries obtained in Examples 1 to 6, and Comparative Examples 1 and 2 were measured for the initial discharge capacity and the discharge capacity retention at 20° C. and 60° C., and tested for the safety by a nail penetration test as follows.

(1) Measurement for Initial Discharge Capacity at 20° C.

The capacity measured after each nonaqueous secondary battery is charged up to 4.2 V at a rate of 0.1 CmA, and then discharged down to 3.0 V at a rate of 0.1 CmA is determined as the initial discharge capacity (mAh/g). The measurement is performed in an incubator set to a constant temperature of 20° C.

(2) Measurement for Discharge Capacity Retention at 20° C.

A cycle of charging each nonaqueous secondary battery up to 4.2 V at a rate of 1 CmA and discharging the battery down to 3.0 V at a rate of 1 CmA is repeated 99 times, and then a cycle of charging and discharging under the same condition as in the measurement for the initial discharge capacity is completed for the 100th time in total, whereupon the battery is measured for the capacity.

After completion of the measurement for the 100th time, a cycle of charging each nonaqueous secondary battery up to 4.2 V at a rate of 1 CmA and discharging the battery down to 3.0 V at a rate of 1 CmA is repeated 499 times, and then a cycle of charging and discharging under the same condition as in the measurement for the initial discharge capacity is completed for the 500th time in total, whereupon the battery is measured for the capacity.

The discharge capacity retention (%) at the 100th cycle and the discharge capacity retention (%) at the 500th cycle are defined as the percentage of the initial discharge capacity accounted for by the discharge capacity at the 100th cycle and the percentage of the initial discharge capacity accounted for by the discharge capacity at the 500th cycle, respectively. The measurement is performed in an incubator set to a constant temperature of 20° C.

(3) Initial Discharge Capacity and Discharge Capacity Retention at 60° C.

The measurement for the initial discharge capacity (mAh/g) and the discharge capacity retention (%) at 60° C. are performed in the same manner as in the measurement for the initial discharge capacity and the discharge capacity retention at 20° C. except that the temperature of the incubator is set to a constant temperature of 60° C.

(4) Nail Penetration Test

As the nail penetration test, a nail having a diameter of 3 mm is driven into each nonaqueous secondary battery having been charged up to 4.2 V at a rate of 0.1 CmA so that the nail penetrates the battery at a speed of 1 mm/s at a room temperature of 20° C. to observe the state of the battery.

Table 1 shows test results together with the constituent materials of the nonaqueous electrolyte solutions and their percentages.

The abbreviations in Table 1 represent the followings:
$LiPF_6$: lithium salt $LiPF_6$
EC/DEC: mixed solvent of ethylene carbonate and diethylene carbonate
A: N-acetoxy-N-methyl-acetamide
B: succuinimidyl acrylate
C: di(N-succinimidyl) carbonate
D: acetoxime benzoate
AIBN: azobisisobutyronitrile

TABLE 1

| | | | Examples | | | | | | Comparative Examples | |
|---|---|---|---|---|---|---|---|---|---|---|
| | | | 1 | 2 | 3 | 4 | 5 | 6 | 1 | 2 |
| Nonaqueous electrolyte solution | Electrolyte salt | Kind | $LiPF_6$ | $LiPF_6$ | $LiPF_6$ | $LiPF_6$ | $LiPF_6$ | $LiPF_6$ | $LiPF_6$ | $LiPF_6$ |
| | Nonaqueous solvent | Kind (volume ratio) | EC/DEC (1/2) | EC/DEC (1/2) | EC/DEC (1/2) | EC/DEC (1/2) | EC/DEC (1/2) | EC/DEC (1/2) | EC/DEC (1/2) | EC/DEC (1/2) |
| | | Percentage (V/V %) | 80 | 99 | 40 | 90 | 90 | 90 | 100 | 98 |
| | | Kind | A | A | A | B | C | D | — | AIBN |
| | | Percentage (V/V %) | 20 | 1 | 60 | 10 | 10 | 10 | — | 2 |
| Electric characteristics (20° C.) | Initial | Discharge capacity (mAh/g) | 118.2 | 120.1 | 116.5 | 118 | 118.3 | 116.9 | 115.3 | 91.2 |
| | $100^{th}$ cycle | Discharge capacity (mAh/g) | 113.5 | 118.9 | 108.3 | 113.3 | 113.6 | 111.0 | 106.1 | 82.1 |
| | | Discharge capacity retention (%) | 96 | 99 | 93 | 96 | 96 | 95 | 92 | 90 |
| | $500^{th}$ cycle | Discharge capacity (mAh/g) | 104.0 | 108.1 | 97.9 | 102.0 | 101.7 | 100.5 | 94.1 | 68.4 |
| | | Discharge capacity retention (%) | 88 | 90 | 84 | 86 | 86 | 86 | 82 | 75 |
| Electric characteristics (60° C.) | Initial | Discharge capacity (mAh/g) | 117.5 | 118.9 | 115.4 | 117.5 | 117.8 | 116.8 | 112.6 | — |
| | $100^{th}$ cycle | Discharge capacity (mAh/g) | 104.6 | 108.2 | 94.6 | 106.1 | 107.2 | 102.8 | 89.0 | — |
| | | Discharge capacity retention (%) | 89 | 91 | 82 | 90 | 91 | 88 | 79 | — |

TABLE 1-continued

|  |  | Examples | | | | | | Comparative Examples | |
|---|---|---|---|---|---|---|---|---|---|
|  |  | 1 | 2 | 3 | 4 | 5 | 6 | 1 | 2 |
| 500th cycle | Discharge capacity (mAh/g) | 94.0 | 97.5 | 83.1 | 95.9 | 94.2 | 91.1 | 68.0 | — |
|  | Discharge capacity retention (%) | 80 | 82 | 72 | 82 | 80 | 78 | 61 | — |
| Nail penetration test |  | None | None | None | None | None | None | Smoke Fire | Smoke Fire |

The results shown in Table 1 have revealed the following:

The general nonaqueous secondary battery using a general organic solvent as a nonaqueous solvent and containing no flame retardant (Comparative Example 1) experienced generation of smoke and generation of fire in the nail penetration test. The nonaqueous secondary battery containing AIBN, which is a general flame retardant, (Comparative Example 2) also experienced generation of smoke and generation of fire in the nail penetration test as in the case of Comparative Example 1.

On the other hand, the nonaqueous secondary batteries in which the nonaqueous solvent contains a compound of the present invention (Examples 1 to 6) did not experience abnormal events such as generation of smoke and generation of fire in the nail penetration test. Furthermore, in terms of the battery performance, the nonaqueous secondary batteries of Examples 1 to 6 produced significantly good results compared with the nonaqueous secondary battery of Comparative Examples 2 containing AIBN, which is a general flame retardant.

In addition, the nonaqueous secondary battery of Comparative Example 2 experienced electrolysis of AIBN in the electrolyte solution during charge and discharge at 20° C. and 60° C., showed deterioration of the cycle characteristic at 20° C., and failed to provide stable electrochemical characteristics at 60° C.

As described above, Table 1 indicates that it is possible to obtain a nonaqueous secondary battery improved in the flame retardancy and comparable in the electric characteristics to a conventional one by using a compound of the present invention as a flame retardant in a nonaqueous electrolyte solution.

What is claimed is:

1. A nonaqueous secondary battery, comprising: a positive electrode; a negative electrode; and a nonaqueous electrolyte solution, the nonaqueous electrolyte solution containing as a flame retardant a compound of the general formula (I):

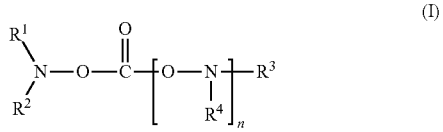

(I)

wherein $R^1$ and $R^2$, which are the same or different, each represents a group that is selected from a hydrogen atom, a lower alkyl, lower alkenyl, lower alkoxy, lower alkoxycarbonyl, lower alkylcarbonyl, lower cycloalkyl or aryl group, and that may have a substituent, or $R^1$ and $R^2$ taken together are a methylene group that may have a substituent, or $R^1$ and $R^2$ taken together form a ring structure containing a nitrogen atom to which $R^1$ and $R^2$ are attached, the ring structure being a five-membered or six-membered hydrocarbon ring that may have one or two oxo groups, or a five-membered or six-membered heterocycle that may further contain a nitrogen atom; n is 1; $R^3$ and $R^4$ are as defined for $R^1$ and $R^2$;

wherein percentage of the compound of the general formula (I) to be blended in the nonaqueous electrolyte solution is in the range of 10% to 40% by volume fraction; and wherein the compound of the general formula (I) is a compound that produces inert gas containing $CO_2$ or $CO$ as a main component when heated at a temperature higher than its decomposition temperature.

2. The nonaqueous secondary battery of claim 1, wherein the compound of the general formula (I) is a compound that has a decomposition temperature from 120° C. to 250° C.

3. A nonaqueous secondary, comprising: a positive electrode; a negative electrode; and a nonaqueous electrolyte solution, the nonaqueous electrolyte solution containing as a flame retardant a compound of the general formula (I):

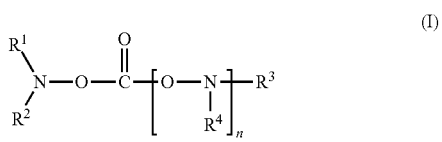

(I)

wherein $R^1$ and $R^2$, which are the same or different, each represents a group that is selected from a hydrogen atom, a lower alkyl, lower alkenyl, lower alkoxy, lower alkoxycarbonyl, lower alkylcarbonyl, lower cycloalkyl or aryl group, and that may have a substituent, or $R^1$ and $R^2$ taken together are a methylene group that may have a substituent, or $R^1$ and $R^2$ taken together form a ring structure containing a nitrogen atom to which $R^1$ and $R^2$ are attached, the ring structure being a five-membered or six-membered hydrocarbon ring that may have one or two oxo groups, or a five-membered or six-membered heterocycle that may further contain a nitrogen atom; n is 1; and $R^3$ and $R^4$ are as defined for $R^1$ and $R^2$, wherein $R^1$ and $R^2$ represent a group that is selected from methyl, tert-butyl, vinyl, methoxy, acetoxy, acetyl, cyclopropyl, cyclobutyl, phenyl, 2-naphthyl and p-tolyl groups, or $R^1$ and $R^2$ taken together are isopropylidene group, or $R^1$ and $R^2$ taken together form a ring structure containing a nitrogen atom to which $R^1$ and $R^2$ are attached, the ring structure formed by succinyl group or being imidazolyl ring, $R^3$ and $R^4$ represent a group that is selected from methyl, tert-butyl, vinyl, methoxy, acetoxy, acetyl, cyclopropyl, cyclobutyl, phenyl, 2-naphthyl and p-tolyl groups, or $R^3$ and $R^4$ taken together are isopropylidene group, or $R^3$ and $R^4$ taken together form a ring structure containing a nitrogen atom to which $R^3$ and $R^4$ are attached, the ring structure being succinimide or imidazole ring; and wherein percentage of the compound of the general formula (I) to be blended in the nonadueous electrolyte solution is in the range of 10% to 40% by volume fraction.

4. The nonaqueous secondary battery of claim 1, wherein the compound of the general formula (I) is di(N-succinimidyl) carbonate or 1,1'-(Carbonylbisoxy)bis(1H-imidazole).

5. The nonaqueous secondary battery of claim 1, wherein the compound of the general formula (I) is di(N-succinimidyl) carbonate.

6. A nonaqueous flame retardant electrolyte solution for a nonaqueous secondary battery comprising a compound of the general formula (I):

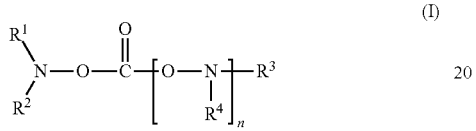

(I)

wherein $R^1$ and $R^2$, which are the same or different, each represents a group that is selected from a hydrogen atom, a lower alkyl, lower alkenyl, lower alkoxy, lower alkoxycarbonyl, lower alkylcarbonyl, lower cycloalkyl or aryl group, and that may have a substituent, or $R^1$ and $R^2$ taken together are a methylene group that may have a substituent, or $R^1$ and $R^2$ taken together form a ring structure containing a nitrogen atom to which $R^1$ and $R^2$ are attached, the ring structure being a five-membered or six-membered hydrocarbon ring that may have one or two oxo groups, or a five-membered or six-membered heterocycle that may further contain a nitrogen atom; n is 1; and $R^3$ and $R^4$ are as defined for $R^1$ and $R^2$; and wherein percentage of the compound of the general formula (I) to be blended in the nonadueous electrolyte solution is in the range of 10% to 40% by volume fraction.

* * * * *